United States Patent [19]

Kapp

[11] 4,347,241
[45] Aug. 31, 1982

[54] DELAYED RELEASE COATED METAL PHOSPHIDE PESTICIDES

[75] Inventor: Wolfgang Kapp, Offenbach am Main, Fed. Rep. of Germany

[73] Assignee: Degesch GmbH, Frankfurt, Fed. Rep. of Germany

[21] Appl. No.: 882,949

[22] Filed: Mar. 1, 1978

Related U.S. Application Data

[63] Continuation-in-part of Ser. No. 716,701, Aug. 19, 1976, abandoned.

[30] Foreign Application Priority Data

Sep. 2, 1975 [ZA] South Africa .................... 75/5587

[51] Int. Cl.³ .................... A01N 55/00; A01N 59/26
[52] U.S. Cl. .................... 424/128; 424/184
[58] Field of Search .................... 424/128, 184, 78

[56] References Cited

U.S. PATENT DOCUMENTS

| | | | |
|---|---|---|---|
| 2,826,486 | 3/1958 | Hüter | 424/128 X |
| 2,826,527 | 3/1958 | Hüter | 424/128 |
| 3,132,067 | 5/1964 | Rauscher et al. | 424/128 X |
| 3,159,536 | 1/1964 | Marotta | 424/128 |
| 3,624,198 | 11/1971 | Arbaugh | 424/17 |
| 3,719,751 | 3/1973 | Rauscher et al. | 424/27 |

FOREIGN PATENT DOCUMENTS 888149 12/1971 Canada .
1542877 7/1970 Fed. Rep. of Germany .

OTHER PUBLICATIONS

Label Registration; Union of South Africa, 9 pages; 6/26/74.

*Primary Examiner*—Allen J. Robinson

[57] ABSTRACT

A pest control product is provided from a metal phosphide particle coated with a water soluble coating that has been rendered water repellent. The coating also contains a material which will chemically or physically disintegrate to cause apertures in the coating to provide access for water to the phosphide particles.

7 Claims, No Drawings

DELAYED RELEASE COATED METAL PHOSPHIDE PESTICIDES

This application is a continuation-in-part of parent application Ser. No. 716,701, filed Aug. 19, 1976, now abandoned.

BACKGROUND OF THE INVENTION

This invention relates to pest control compositions containing a metal phosphide which is capable of reacting with water, under the conditions of use, to release phosphine, and is particularly concerned with compositions which exhibit a controlled rate of hydrolysis of the phosphide.

SUMMARY OF THE INVENTION

According to the present invention there is provided a composition for pest control purposes which includes a metal phosphide suitable for pest control purposes, coated with a solid substance which has been rendered water-repellent, the coating including a substance which is capable of being chemically or physically modified or decomposed to cause apertures to be formed in the coating under predetermined conditions, for access of water or water vapor to the phosphide particles.

In the preferred form of the invention the metal phosphide is aluminum phosphide but it will be appreciated that other phosphides such as magnesium and calcium phosphide may also be used for certain pest control applications.

Thus attention is directed to Huter U.S. Pat. No. 2,826,527, the entire disclosure of which is hereby incorporated by reference and relied upon.

In the present invention, a solid coating substance is preferably a compound such as urea which, by itself is a useful coating substance but which is, of course, water-soluble. Thus, it is necessary to render it water-repellent and this is done, according to the invention, by mixing it with a suitable polysiloxane in the presence of a organometallic catalyst.

The amount of polysiloxane to be reacted on the surface of the urea will depend upon the final properties of the composition desired. Obviously, the more polysiloxane there is, the more urea will be rendered hydrophobic and the more efficient the coating will be insofar as water-repellency is concerned. Usually the polysiloxane is 4 to 18% based on the weight of the urea.

In the practice of this invention, solid particulate urea is first mixed with poly(methylhydrogensiloxane) in a solvent such as carbon tetrachloride together with an organometallic catalyst such as dibutyl tin dilaurate in carbon tetrachloride followed by heating and stirring for about an hour at 120° C. (the urea, of course, is insoluble in such solvent). While not being limited by theory, the resulting reaction is believed to involve the combination of atmospheric oxygen atoms with the hydrogen atoms of the polysiloxane, and liberation of water molecules to give Si-O-Si cross-linking groupings. Another possible reaction is the hydrolytic splitting off of the hydrogen atoms joined to silicon atoms by absorption of water vapor from the atmosphere with release of hydrogen and the formation again of the grouping Si-O-Si. Whatever the reaction, a high molecular weight product results which adheres to the surface of the urea crystal particles.

It will be understood from the foregoing description that this invention thus contemplates a catalyzed reaction of the polysiloxane material in the presence of a catalyst while being mixed with particulate urea in order to coat and hydrophobize the latter so as to render it water-repellent. The resulting urea-siloxane composition may then serve as a coating substance to coat the decomposable substance, and, in turn, the phosphide, mentioned above, whereby the reaction of the same with water or water vapor will be delayed until apertures or cracks appear in such coating.

To achieve these results it is critical that the urea be mixed with polysiloxane in the presence of the catalyst and air, as described, before the urea-polysiloxane product is dry-mixed with the decomposable substance and with the above-described phosphide all for the coating of the latter two components of the final pesticide composition provided by this invention.

Besides dibutyl tin dilaurate as catalyst there is generally required a low valence state noble transition metal coordination compound or other known hydrogenation, dehydrogenation and oxygenation catalysts of the noble transition metals of Group VIII of the Periodic Table in the form of organometallic coordination compounds illustrated by the following species:

Tris(triphenylphosphine)chloro-rhodium (I); e.e., $Rh(P(C_6H_5)_3)_3Cl$;

Bis(triphenylphosphine)carbonylchloro-iridium (I); i.e., $Ir(P(C_6H_5)_3)_2COCl$.

Tris(triphenylphosphine)chloro(dioxygen)-rhodium (I); i.e., $RH(P(C_6H_5)_3)Cl(O_2)$;

Bis(triphenylphosphine)chloro(carbonyl)(dioxygen)-iridium (I); i.e., $Ir(P(C_6H_5)_3)_2Cl(CO)(O_2)$; and Dicobaltoctacarbonyl; i.e., $Co_2(CO)_8$.

Other solvents which may be employed include dichloromethane, chloroform, benzene, toluene, etc., or mixtures thereof. In general, non-polar organic solvents for the polysiloxane may be employed which are inert to the catalyst employed and in which urea is itself insoluble.

The decomposable substance itself can be ammonium carbamate, as this material advantageously decomposes into ammonia and carbon dioxide under conditions existing in, for instance, grain silos. The release of these two gases causes the coating to crack and apertures are formed therein which then permit access of water and/or water vapor to the aluminum phosphide, or other phosphide particles.

Other decomposable materials which can similarly be used include ammonium carbonate, sodium bicarbonate, ammonium bicarbonate, ammonium cyanide and potassium bicarbonate.

As is described in U.S. Pat. No. 2,826,527, the resulting composition is usually compressed to form pellets or tablets for actual use.

There is thus created for the compositions in use, an initial delay period before appreciable quantities of phosphine are released. This delay gives the user time to locate and place the tablets and leave the premises to be fumigated before dangerous quantities of phosphine are present. Naturally, the rate of release of phosphine will depend on many factors such as ambient temperature, the humidity, the care or lack of care with which the tablets have been transported or opened, and so on. Naturally, also, the normal precautions associated with the handling of phosphide compositions, e.g., aluminum phosphide compositions must be observed.

DESCRIPTION OF THE PREFERRED EMBODIMENTS

Typical examples of compositions according to the invention are set forth below.

Solution 1

10 g polymethylhydrogensiloxane (Goldschmidt P.T.F.1) is dissolved in 100 ml carbon tetrachloride.

Solution 2

100 mg dibutyltindilaurate is dissolved in 100 ml. carbon tetrachloride.

EXAMPLE A 12 ml of Solution 1 is mixed with 10 ml of Solution 2 and 20 g urea.

EXAMPLE B 14 mol. of Solution 1 is mixed with 10 ml of Solution 2 and 20 g urea.

EXAMPLE C 16 ml of Solution 1 is mixed with 10 ml of Solution 2 and 20 g urea.

EXAMPLE D 18 ml of Solution 1 is mixed with 10 ml of Solution 2 and 20 g urea.

Tablets are made using 20.5 gm. of urea treated in each of these Examples, with 69.5 gm of technical aluminum phosphide and 10 gm ammonium carbamate.

The following Table shows the amount of available phosphine present in the products of the Examples as a function of time in hours.

The measurements were made at 20° C. and 70% humidity.

TABLE

| Hours | Example A | Example B | Example C | Example D |
| --- | --- | --- | --- | --- |
| 0 | 31.7 | 30.8 | 31.9 | 31.8 |
| 1 | 31.8 | 30.8 | 31.5 | 30.6 |
| 2 | 30.9 | 30.7 | 31.4 | 30.0 |
| 3 | 30.3 | 30.5 | 30.3 | 28.6 |
| 4 | 28.1 | 29.6 | 29.6 | 28.1 |
| 5 | 26.0 | 25.2 | 26.1 | 25.9 |
| 24 | 4.4 | 3.4 | 3.6 | 3.5 |
| 48 | 1.75 | 1.77 | 1.75 | 1.70 |
| 72 | 1.67 | 1.57 | 1.64 | 1.55 |

As indicated in the cited Huter patent, the amount of coating material can vary within wide ranges, e.g., the coated tablets can contain in addition to the phosphide 10 to 80% of the hydrophobized water soluble solid, e.g., urea, and the decomposable material. The decomposable material normally is not itself hydrophobized.

Following the procedures of the foregoing Examples, the other catalysts or other solvents, named above may also be used, with good results. For instance, use of the dicobaltoctacarbonyl compound showed comparable results to the dibutyl-tin-dilaurate compound, while the rhodium and iridium compounds named above actually are superior in performance to the tin compound.

Thus, as a further Example, 15 ml of a solution of polymethyl hydrogen siloxane (10 gm) in 100 ml of dichloromethane was mixed with 3.8 ml of a 0.2% solution $Rh(P(C_6H_5)_3)_3Cl$, also in dichloromethane, to which was added 19 gm of finely divided crystal urea. The mixture was stirred at 24° C. for 3 hours, in contact with air while the solvent volatilized. The solid was then dry-mixed with 69.5 gm Technical Grade aluminum phosphide and 10 gm of ammonium carbamate, after which the solid mixture was compressed to form tablets of 3 gm weight each.

Upon exposure to air of 70% humidity at 20° C., the amount of phosphine remaining in the tablet as a function of time was measured as follows:

| Hours | % Phosphine in Tablet |
| --- | --- |
| 0 | 33.8 |
| 1 | 33.8 |
| 2 | 32.7 |
| 3 | 31.5 |
| 4 | 30.5 |
| 5 | 29.3 |
| 12 | 14.4 |
| 24 | 5.0 |

What is claimed is:

1. A composition for pest control by fumigation including a metal phosphide, selected from the group consisting of aluminum phosphide, magnesium phosphide and calcium phosphide, dry-coated with a composition composed of urea, which urea has first been rendered water-repellent by treatment in a non-polar organic solvent with a water-repellent poly(methyl hydrogen)siloxane substance in the presence of air and an organometallic catalyst of a noble transition metal of Group VIII of the Periodic Table, or of tin, said coating composition also including a substance which is chemically or physically modifiable or decomposable to cause apertures to be formed in the coating under predetermined conditions for access of water or water vapor to the phosphide particles, said modifiable or decomposable substance being selected from the group consisting of ammonium carbamate, ammonium carbonate, sodium bicarbonate, ammonium bicarbonate, ammonium cyanide and potassium bicarbonate.

2. The composition of claim 1 wherein the metal phosphide is aluminum phosphide.

3. In a tablet for pest control for fumigation, said tablet including a metal phosphide selected from the group consisting of aluminum phospide, magnesium phosphide and calcium phosphide and a coating substance which can be decomposed to cause apertures to be formed in the tablet for access to the phosphide, said substance including a member selected from the group consisting of ammonium carbamate, ammonium carbonate, sodium bicarbonate, ammonium bicarbonate, ammonium cyanide and potassium bicarbonate, the improvement comprising employing as the coating for the metal phosphide a composition of urea which has first been rendered water-repellent by treatment in a non-polar organic solvent a water-repellent poly(methyl hydrogen)siloxane in the presence of air and an organometallic catalyst of a noble transition metal of Group VIII of the Periodic Table, or of tin, which coating composition is dry-mixed with said phosphide to coat the same.

4. A tablet consisting of the materials set forth in claim 1.

5. A tablet according to claim 4 wherein the urea is coated with 4 to 18% of its weight said polysiloxane.

6. A method of preparing a controlled-release pesticide consisting essentially in mixing a solution in a non-polar organic solvent of poly(methyl hydrogen)siloxane with a catalytically active organometallic compound of a noble transition metal of Group VIII of the Periodic Table, or of tin, together with particulate solid urea crystals in the presence of atmospheric oxygen to form a poly(methyl hydrogen)siloxane hydrophobized urea composition, and thereafter dry-mixing a metal phosphide and a decomposable gas-release substance with said hydrophobized urea composition to form a coated metal phosphide composition.

7. The process according to claim 6, further including the step of compressing said composition into a molded body of the form of a tablet.

* * * * *